(12) United States Patent
Nishida et al.

(10) Patent No.: US 8,574,509 B2
(45) Date of Patent: Nov. 5, 2013

(54) SENSOR HOLDER, HOLDER UNIT IN WHICH BLOOD SENSOR IS MOUNTED TO THE SENSOR HOLDER, AND BLOOD TESTING DEVICE TO WHICH THE HOLDER UNIT IS MOUNTED

(75) Inventors: Takeshi Nishida, Fukuoka (JP); Tetsuya Takashima, Ehime (JP); Yohei Hashimoto, Ehime (JP)

(73) Assignee: Panasonic Corporation, Osaka (JP)

( * ) Notice: Subject to any disclaimer, the term of this patent is extended or adjusted under 35 U.S.C. 154(b) by 251 days.

(21) Appl. No.: 12/632,141

(22) Filed: Dec. 7, 2009

(65) Prior Publication Data

US 2010/0150777 A1 Jun. 17, 2010

(30) Foreign Application Priority Data

Dec. 17, 2008 (JP) .................................. 2008-320444

(51) Int. Cl.
*G01N 33/48* (2006.01)
*G01N 33/00* (2006.01)
*B01L 9/00* (2006.01)

(52) U.S. Cl.
USPC .............................. 422/400; 422/50; 422/68.1

(58) Field of Classification Search
USPC .................................................. 422/68.1, 50
See application file for complete search history.

(56) References Cited

U.S. PATENT DOCUMENTS

| 4,790,979 | A | * | 12/1988 | Terminiello et al. | ........... 422/410 |
| 5,509,410 | A | * | 4/1996 | Hill et al. | ........... 600/393 |
| 6,027,459 | A | * | 2/2000 | Shain et al. | ........... 600/573 |
| 6,071,249 | A | | 6/2000 | Cunningham et al. | |
| 6,071,251 | A | | 6/2000 | Cunningham et al. | |
| 6,093,156 | A | | 7/2000 | Cunningham et al. | |
| 2003/0212345 | A1 | * | 11/2003 | McAllister et al. | ........... 600/584 |

FOREIGN PATENT DOCUMENTS

| JP | 2001-515377 | 9/2001 |
| WO | 98/24366 | 6/1998 |

* cited by examiner

*Primary Examiner* — Christine T Mui
(74) *Attorney, Agent, or Firm* — Wenderoth, Lind & Ponack, L.L.P.

(57) ABSTRACT

A sensor holder comprises a sensor mounting part having a first face on which a blood sensor is placed, a second face provided on the opposite side from the first face, and a through-hole that goes from the first face to the second face and is large enough to allow a laser beam to pass through; a finger holding part that is provided on the second face and surrounds the through-hole, and a grip that sticks out from the blood testing device when the sensor holder is mounted to the blood testing device.

11 Claims, 15 Drawing Sheets

SENSOR HOLDER, HOLDER UNIT IN WHICH BLOOD SENSOR IS MOUNTED TO THE SENSOR HOLDER, AND BLOOD TESTING DEVICE TO WHICH THE HOLDER UNIT IS MOUNTED

CROSS REFERENCE TO RELATED APPLICATIONS

This application is based upon and claims the benefit of priority from prior Japanese Patent Application No. 2008-320444, filed on Dec. 17, 2008; the entire contents of which are incorporated herein by reference.

BACKGROUND ART

1. Field of the Invention

The present invention relates to a sensor holder, to a holder unit in which a blood sensor is mounted to the sensor holder, and to a blood testing device to which the holder unit is mounted.

2. Description of the Related Art

A conventional blood testing device (see national publication JP 2001-515377, for example) will now be described. As shown in FIG. 1, the conventional blood testing device 1 comprises a main body 2 having an elliptical cylindrical shape, and a lid 3 that is fitted to the main body 2. The main body 2 comprises a guide 4 that is provided on an end face of the main body 2 and guides the fitting of the lid 3, a connector 5 provided to the guide 4, a blood sensor 6 provided so that it can be inserted into and removed from the connector 5, an electrical circuit (not shown) connected to the connector 5, a display 8 connected to the electrical circuit, a battery (not shown) that supplies power to the circuits of these components, and a needle puncture means 10 provided near the guide 4 and provided in the approximate center of the end face of the main body 2.

The lid 3 comprises a through-hole 11 into which a puncture needle 10a provided to the needle puncture means 10 is inserted, and a finger holding part 12 that surrounds the through-hole 11.

The method for operating the blood testing device 1 constituted in this way will now be described. First, the lid 3 is removed from the main body 2. A new puncture needle 10a and a new blood sensor 6 are then mounted. Once the mounting of the new puncture needle 10a and the new blood sensor 6 is complete, the lid 3 is fitted to the main body 2.

Next, the blood testing device 1 is held in one hand (not shown), and a finger to be punctured (not shown) of the other hand (not shown) is placed against the finger holding part 12. A puncture button (not shown) is then pressed. When the puncture button is pressed, the puncture needle 10a goes through the through-hole 11 and punctures the skin (not shown) of the figure to be punctured. Blood (not shown) oozes out from the skin. This blood is taken into the blood sensor 6, which is set ahead of time near the finger to be punctured. In the blood sensor 6, the blood reacts with a reagent held inside the blood sensor 6. This reaction is electrochemically detected as a current, which is inputted to the electrical circuit, and the blood glucose level or the like is calculated by the electrical circuit. The calculated blood glucose level or the like is displayed on the display 8.

Once the measurement of blood glucose level or the like is thus concluded, the lid 3 is taken off the main body 2 again. The used blood sensor 6 is then removed from the connector 5 and discarded.

BRIEF SUMMARY OF THE INVENTION

With the conventional blood testing device 1, when the used blood sensor 6 is discarded, the user must hold the blood testing device 1 with the one hand and take out the blood sensor 6 with the other hand. This removal of the blood sensor 6 inevitably requires that the punctured finger on the other hand is moved at least once from the finger holding part 12. That is, when puncture is complete, the punctured finger must be moved from the finger holding part 12, and during this movement blood may be deposited near the finger holding part 12. Depositing blood at the finger holding part 12 is unsanitary and can lead to problems such as infection.

The present invention solves this problem, and it is an object thereof to provide a sensor holder with which the deposition of blood can be suppressed, a holder unit in which a blood sensor is mounted in the sensor holder, and a blood testing device in which the holder unit is mounted.

The sensor holder used in the blood testing device of the present invention for achieving this object is a sensor holder that is removably mounted to a blood testing device having a puncture function, and comprises a sensor mounting part having a first face on which a blood sensor is placed, a second face provided on the opposite side of the first face, and a through-hole that goes from the first face to the second face and is large enough to allow a puncture tool to pass through; a finger holding part that is provided on the second face and surrounds the through-hole when seen from the second face side; and a grip that sticks out from the blood testing device when the sensor holder is mounted in the blood testing device.

DETAILED DESCRIPTION OF THE INVENTION

Embodiment 1

Figure 2A:
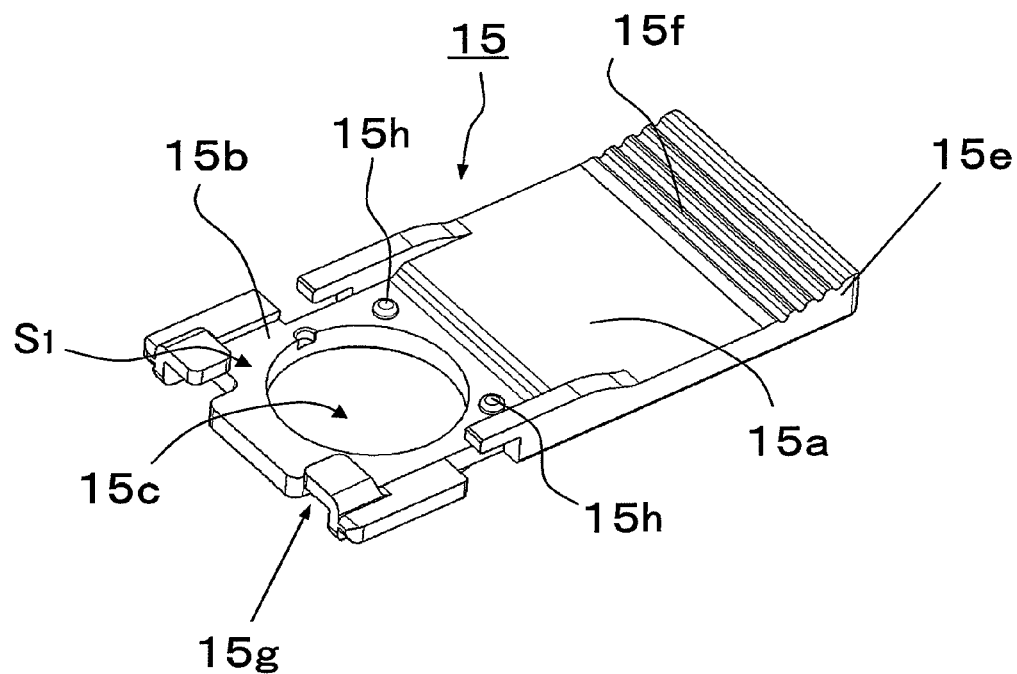
FIG. 2A is an oblique view of a sensor holder 15 pertaining to Embodiment 1, as seen from a first face side.
Figure 2B:
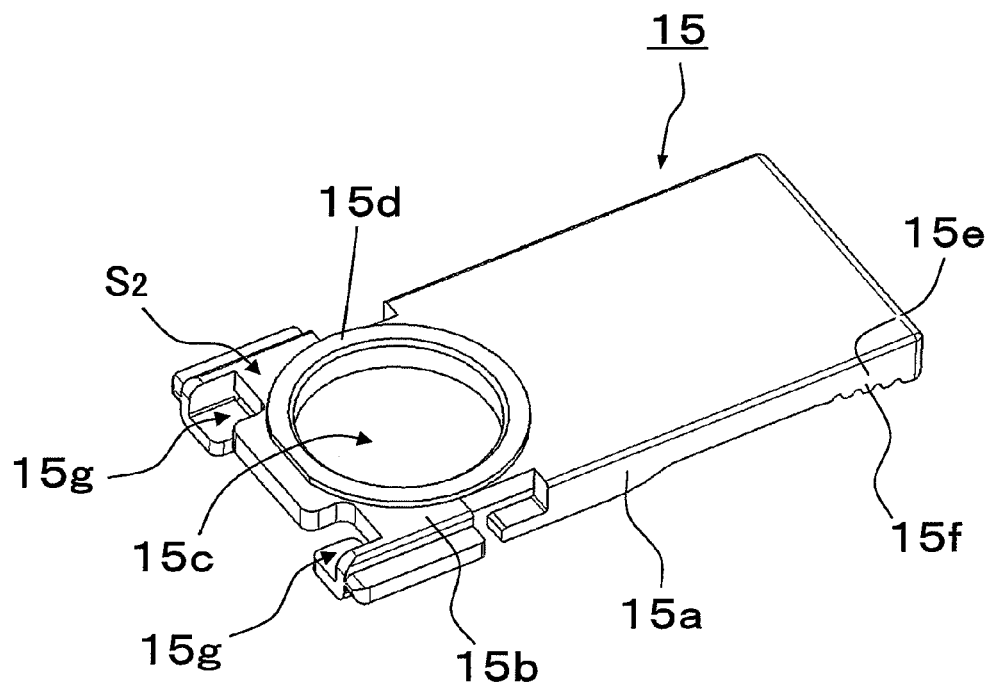
FIG. 2B is an oblique view of the sensor holder 15 pertaining to Embodiment 1, as seen from a second face side.
Figure 2C:
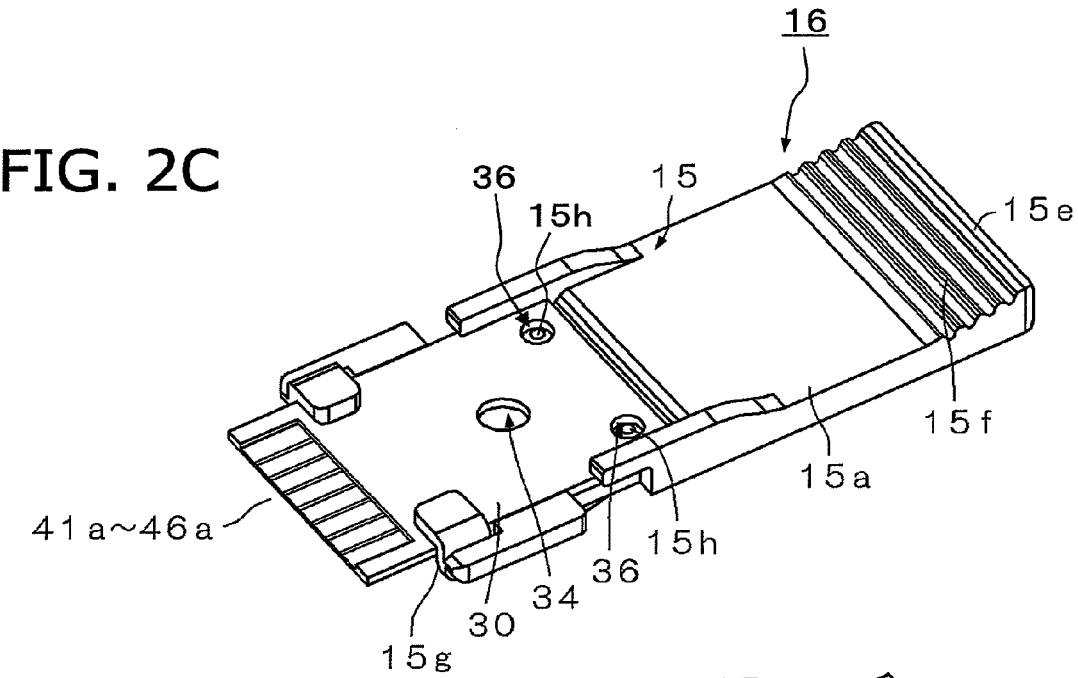
FIG. 2C is an oblique view of a holder unit 16 pertaining to Embodiment 1, as seen from the first face side.
Figure 2D:
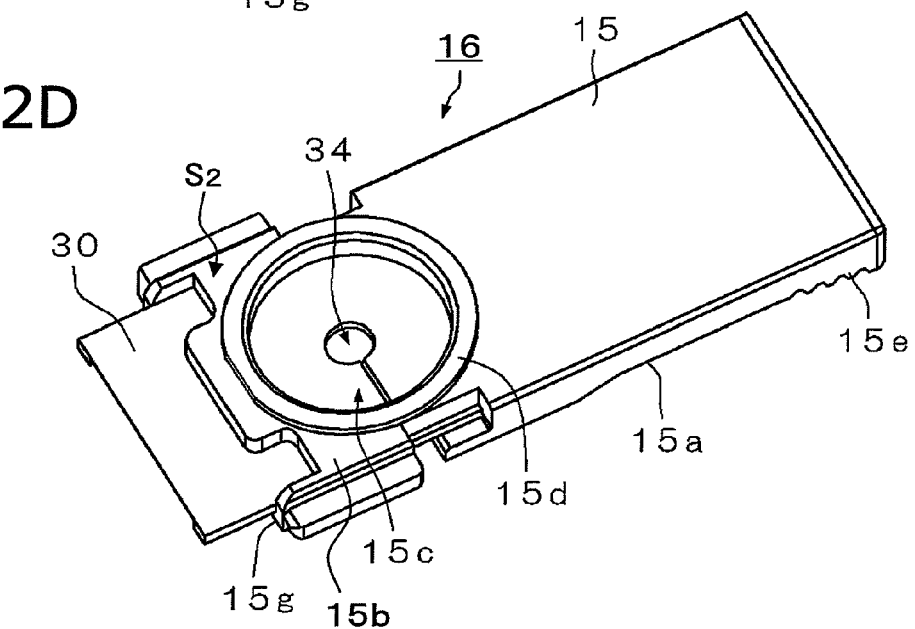
FIG. 2D is an oblique view of the holder unit 16 pertaining to Embodiment 1, as seen from the second face side.

FIG. 2A is an oblique view of a sensor holder 15 pertaining to Embodiment 1, as seen from one side (a first face side), and FIG. 2B is an oblique view of the sensor holder 15 as seen from the other side (a second face side). FIG. 2C is an oblique view of a holder unit 16 pertaining to Embodiment 1, as seen from one side (the first face side), and FIG. 2D is an oblique view of the holder unit 16 as seen from the other side (the second face side). The holder unit 16 is such that a blood sensor 30 is mounted to the sensor holder 15.

As shown in FIGS. 2A to 2D, the sensor holder 15 is formed from a main body center part 15a, a sensor mounting part 15b that is provided at one end of the main body center part 15a and on which the blood sensor 30 is placed, a finger holding part 15d provided on the opposite side of the blood sensor 30 across the sensor mounting part 15b, and a grip 15e provided at the other end of the main body center part 15a.

As shown in FIGS. 2A and 2B, the sensor mounting part 15b has a first face $S_1$ on which the blood sensor 30 is placed, a second face $S_2$ provided on the opposite side from the first face $S_1$, and a through-hole 15c that goes from the first face $S_1$ to the second face $S_2$.

As shown in FIGS. 2C and 2D, the through-hole 15c is provided at a location that lines up with a blood inlet 34 of the blood sensor 30. The through-hole 15c is large enough to allow a puncture tool such as a needle or a laser beam to pass through. The size of the opening of the through-hole 15c is about 3 mm to 12 mm in diameter, which is affected by the size of the finger holding part 15d provided on the second face $S_2$.

Figure 14A:
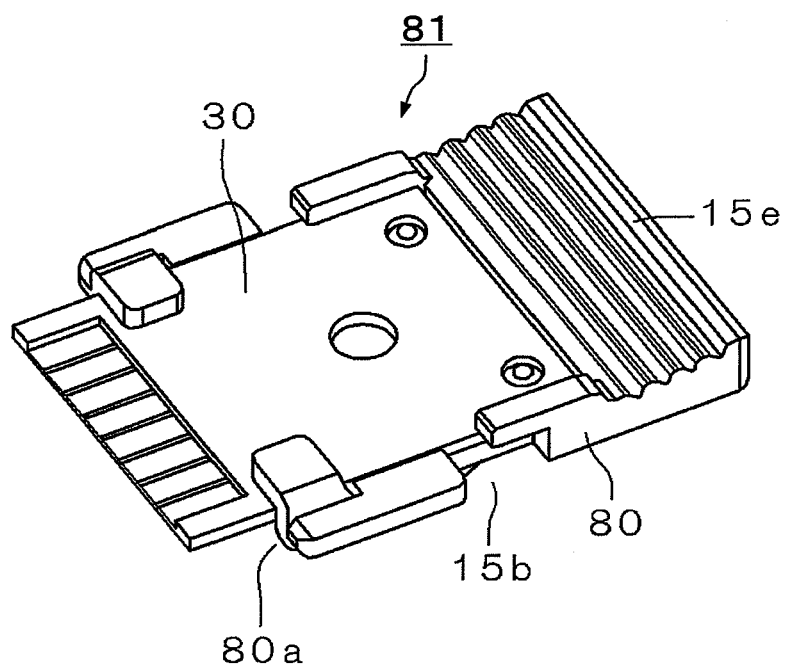
FIG. 14A is an oblique view of a holder unit 81 pertaining to Embodiment 4.

Here, the sensor holder 15 is formed from a rectangular plate, but it is not restricted to being rectangular, as long as it has the sensor mounting part 15b and the finger holding part 15d. The width of the sensor holder 15 may be slightly greater than the outside diameter of the finger holding part 15d. The length of the sensor holder 15 is preferably about twice the length of the blood sensor 30, but it may be just slightly longer than the blood sensor 30, as long as the grip 15e can be formed, as shown in FIG. 14A.

Convex portions 15f are formed in a linear shape on the front side of the grip 15e to limit finger slippage, but are not limited to this shape. For example, the convex portions 15f may have some other shape, such as a zigzag pattern. Also, concave components may be formed instead of the convex portions 15f on the grip 15e, or a surface treatment may be performed that will limit finger slippage.

Insertion openings 15g of the blood sensor 30 are provided at one end of the sensor mounting part 15b, and two latching protrusions 15h are formed on the bottom face of the sensor mounting part 15b. These latching protrusions 15h are latched in latching holes 36 formed in the blood sensor 30. The positions the blood sensor 30 with respect to the sensor mounting part 15b. Also, the latching protrusions 15h are formed with a trapezoidal or semicircular shape, which facilitates the insertion and the removal of the blood sensor 30 from the direction of the insertion openings 15g. However, the blood sensor 30 may be fixed to the sensor holder 15 by some other method. For instance, the blood sensor 30 may be held down by a spring or plate instead of using the latching protrusions 15h.

As shown in FIGS. 2B and 2D, the finger holding part 15d is formed in an annular shape on the second face $S_2$ of the sensor mounting part 15b. The finger holding part 15d surrounds the through-hole 15c as seen from the second face $S_2$ side. The finger holding part 15d serves to fix a first finger 18a (see FIG. 4B to 4D) and to compress the first finger 18a when the first finger 18a is placed against the finger holding part 15d.

Also, as shown in FIG. 2C, connecting electrodes 41a to 46a (see FIG. 7) are formed on the surface of the blood sensor 30.

Figure 3A:
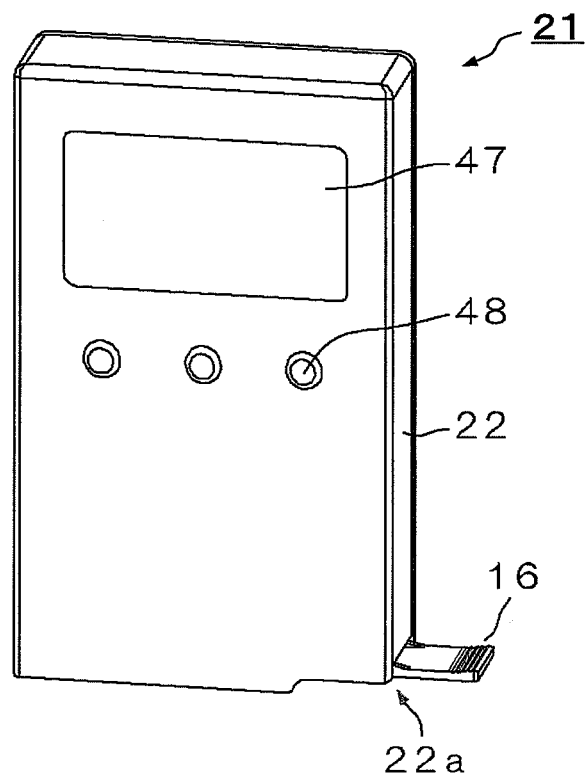
FIG. 3A is an oblique view of a blood testing device 21 pertaining to Embodiment 1, as seen from the front face side.
Figure 3B:
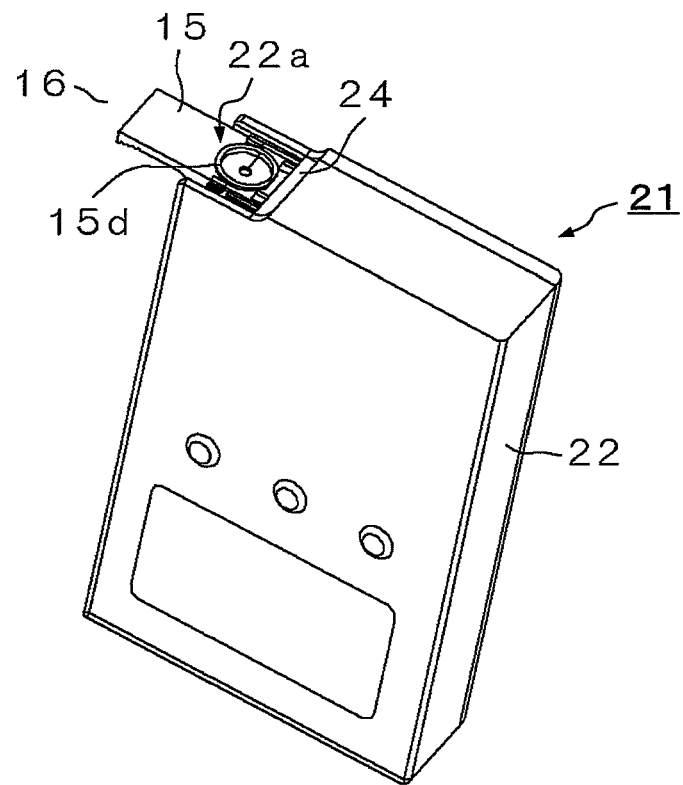
FIG. 3B is an oblique view of the blood testing device 21 pertaining to Embodiment 1, as seen from the bottom face side.

FIG. 3A is an oblique view of a blood testing device 21 to which is mounted the holder unit 16 pertaining to this embodiment, as seen from the front face side. FIG. 3B is an oblique view of the blood testing device 21 to which is mounted the holder unit 16 pertaining to this embodiment, as seen from the bottom face side. As shown in FIG. 3A, the blood testing device 21 is substantially cuboid in shape. A liquid crystal display 47 is provided near the top on one side of the blood testing device 21. Control buttons 48 are provided under the display 47. An opening 22a into which the holder unit 16 is inserted is provided at the lower right corner of a case 22.

As shown in FIG. 3B, connectors 24 (24a to 24f; see FIG. 10) are mounted in the opening 22a. These connectors 24 are connected to the connecting electrodes 41a to 46a of the blood sensor 30 (see FIG. 7). The finger holding part 15d formed on the rear face side of the sensor holder 15 is exposed below the blood testing device 21.

Figure 4A:
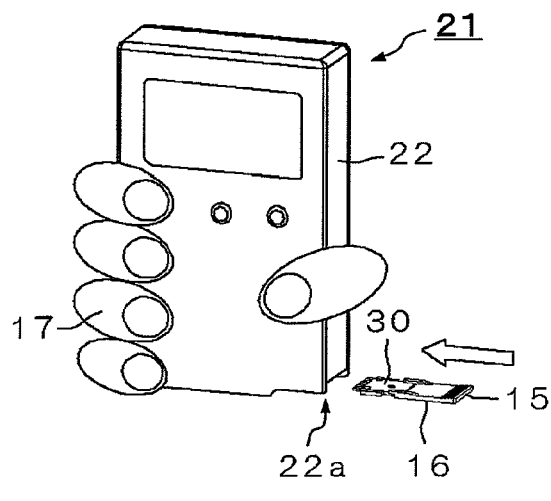
FIG. 4A is an oblique view illustrating how to operate the blood testing device 21 pertaining to Embodiment 1.
Figure 4C:
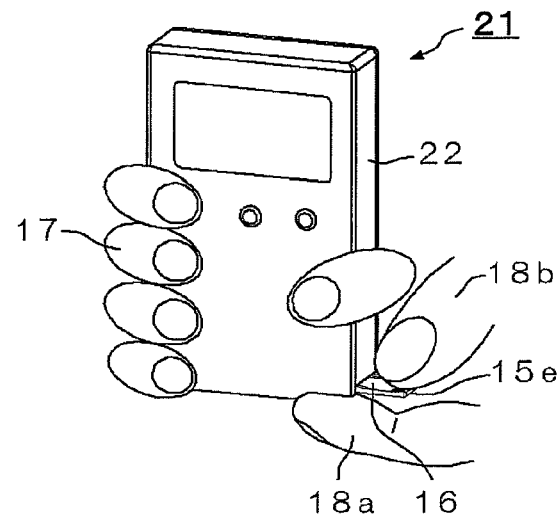
FIG. 4C is an oblique view illustrating how to operate the blood testing device 21 pertaining to Embodiment 1.
Figure 4B:
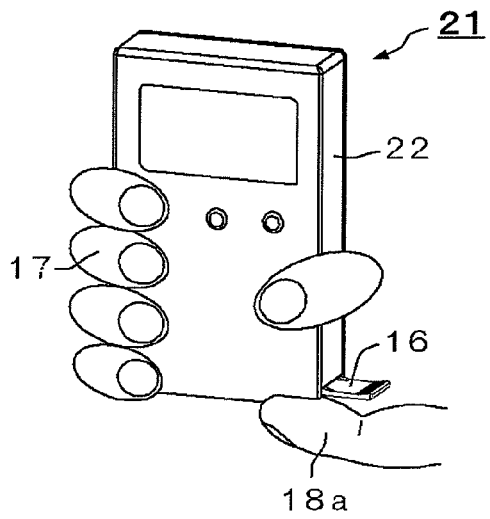
FIG. 4B is an oblique view illustrating how to operate the blood testing device 21 pertaining to Embodiment 1.

FIG. 4A to 4D are oblique views illustrating how to operate the blood testing device 21. First, as shown in FIG. 4A, the user or test subject grasps the blood testing device 21 in one hand 17, and then inserts the holder unit 16, in which the blood sensor 30 is mounted to the sensor holder 15, in the opening 22a. As shown in FIG. 4B, the first finger 18a (such as the index finger) of the other hand 18 is placed against the finger holding part 15d (see FIG. 3). In this state the first finger 18a is punctured. A component (such as the blood glucose level) of the blood 14 (see FIG. 9) that has oozed out as a result of the puncture is then measured.

Figure 4D:
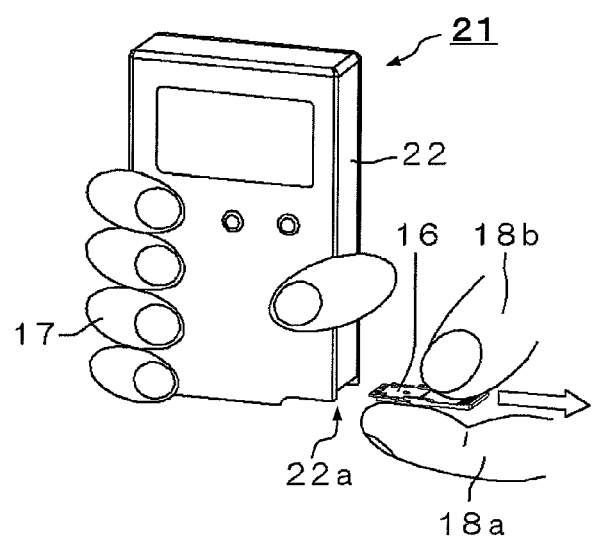
FIG. 4D is an oblique view illustrating how to operate the blood testing device 21 pertaining to Embodiment 1.

As shown in FIG. 4C, after the measurement is completed, a second finger 18b (such as the thumb) of the other hand 18 is placed on the grip 15e, and the holder unit 16 is gripped between the first finger 18a (still touching the finger holding part 15d) and the second finger 18b. Then, as shown in FIG. 4D, the holder unit 16 gripped by the first finger 18a and the second finger 18b is pulled out of a holder unit mounting component 23 (see FIG. 5). Thus, the holder unit 16 can be gripped and pulled out by the first finger 18a and the second finger 18b without moving the first finger 18a. This means that there is no movement of first finger 18a to which the blood 14 clings, and the blood 14 that has oozed out after puncture will tend not to be deposited anywhere else. Therefore, measurement can be carried out more hygienically. Also, the blood sensor 30 to which the blood 14 clings is pulled out of the blood testing device 21 along with the holder unit 16. Accordingly, deposition of the blood 14 on the blood testing device 21 can be suppressed, and the blood testing device 21 can be kept sanitary at all times.

Figure 5:
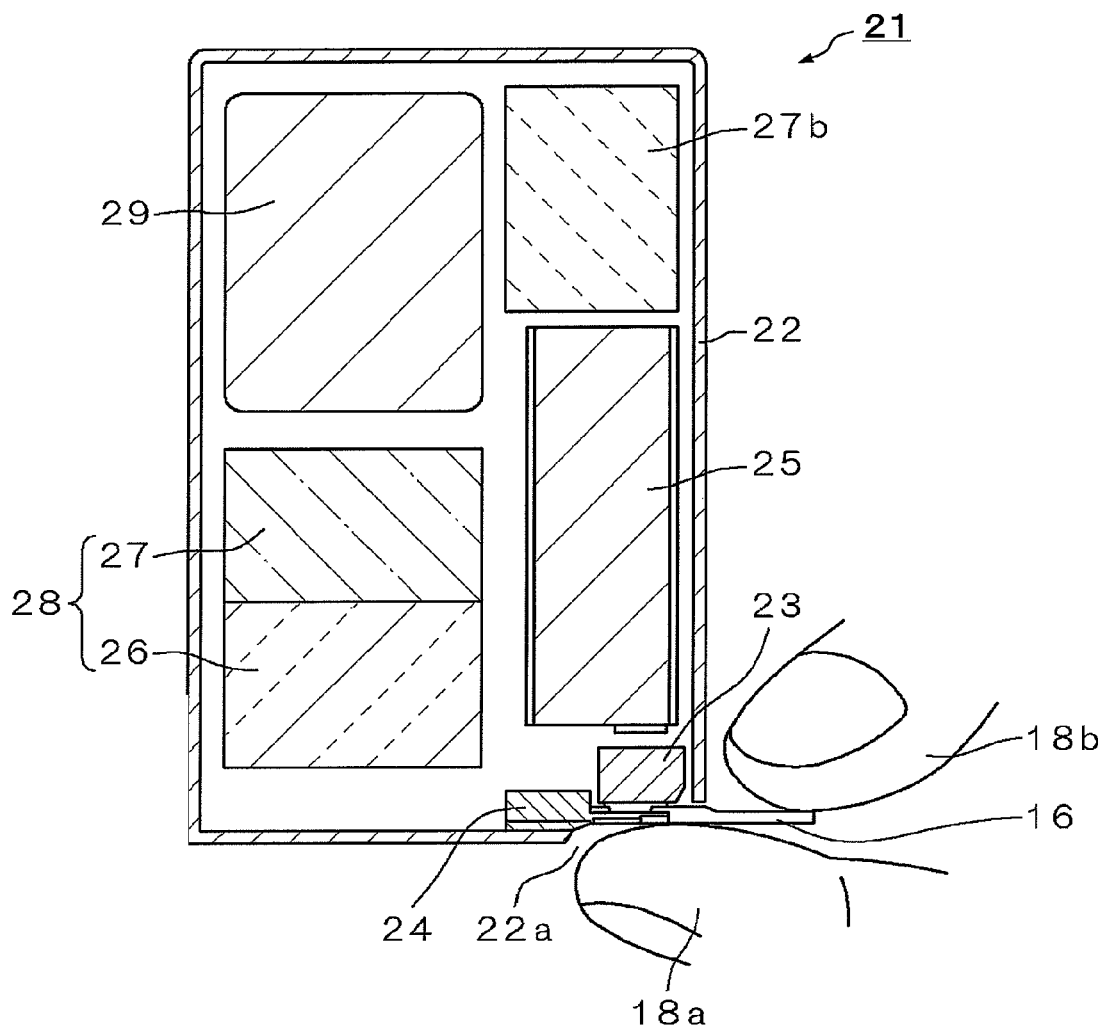
FIG. 5 is a cross section of the blood testing device 21 pertaining to Embodiment 1.

FIG. 5 is a cross section of the blood testing device 21. As shown in FIG. 5, a case 22 has an external shape that is substantially cuboid. The opening 22a is formed at the lower right corner of the case 22, and the holder unit mounting component 23 is provided in the opening 22a. A hole (not shown) through which a laser beam 25e (see FIG. 9) passes is provided in the middle of the holder unit mounting component 23. Rails that support both side faces of the holder unit 16 are also provided to the holder unit mounting component 23. The connectors 24 (24a to 24f; see FIG. 10), into which the connecting electrodes 41a to 46a of the blood sensor 30 (see FIG. 7) are inserted when the holder unit 16 has been inserted, are provided on the opposite side of the holder unit 16 across the opening 22a.

Figure 1:
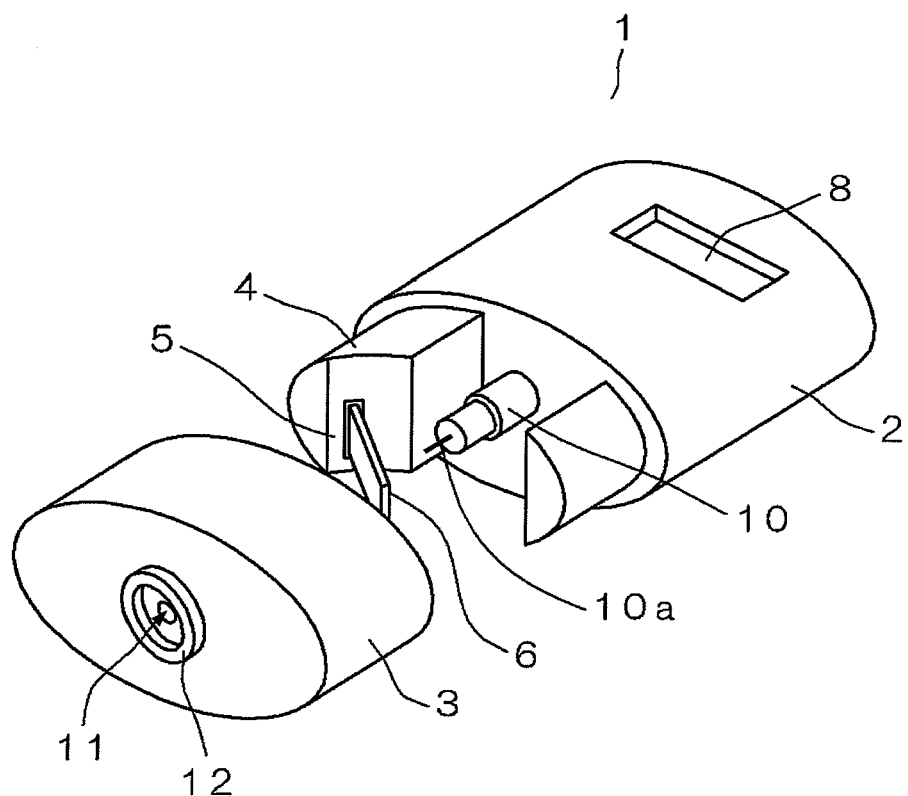
FIG. 1 is an oblique view of a conventional blood testing device 1.

The laser puncture unit 25 (used as an example of a puncture means) is provided on the opposite side of the opening 22a across the holder unit mounting component 23. An electrical circuit 28 including the measurement circuit 26 and the high voltage generation circuit 27 is mounted next to the laser puncture unit 25. The measurement circuit 26 is connected to the connectors 24. Because of its large size and capacity, as shown in FIG. 5, a capacitor 27b that constitutes part of the high voltage generation circuit 27 is disposed above the laser puncture unit 25 and away from the electrical circuit 28, but does not necessarily have to be disposed above the laser puncture unit 25. Also, a battery 29 for supplying power to these components is removably held above the electrical circuit 28. In this embodiment, the laser puncture unit 25 that emits the laser beam 25e (see FIG. 10) is used, but other options are also possible. For instance, a needle puncture means 10 equipped with a puncture needle 10a (see FIG. 1) may be used in place of the laser puncture unit 25.

Figure 6:
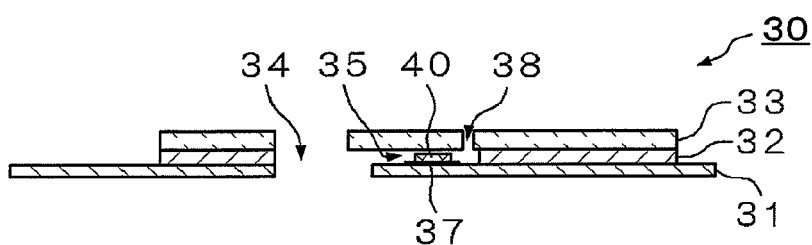
FIG. 6 is a cross section of a blood sensor 30 pertaining to Embodiment 1.

FIG. 6 is a cross section of the blood sensor 30 mounted to the sensor mounting part 15b. The blood sensor 30 comprises a substrate 31, a spacer 32, and a cover 33. The blood inlet 34 is provided passing through the approximate center of the substrate 31.

A film that transmits the laser beam 25e (see FIG. 10) emitted from the laser puncture unit 25 may also be provided to the upper face of the blood sensor 30 (not shown). This reduces the amount of volatile materials caused by laser puncture, blood, and so forth that get in above the blood sensor 30, that is, into the main body of the blood testing device 21.

A supply path 35 is a supply path for the blood 14, and one end of the supply path 35 is linked to the blood inlet 34, and guides the blood 14 accumulated at the blood inlet 34 to a detector 37 all at once by capillary action. The other end of the supply path 35 is linked to an air hole 38.

Figure 7:
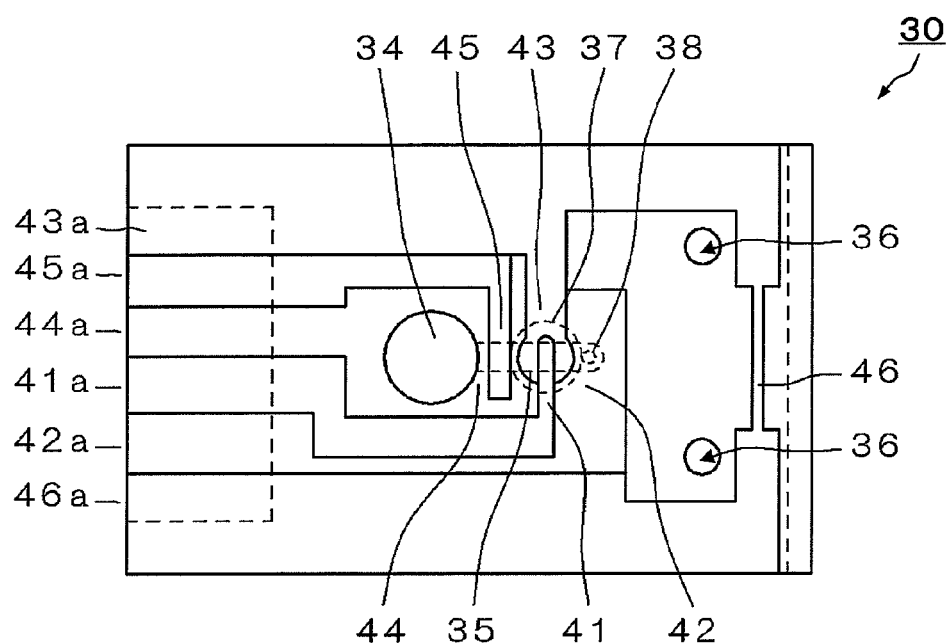
FIG. 7 is a see-through plan view of the blood sensor 30 pertaining to Embodiment 1.
Figure 8:
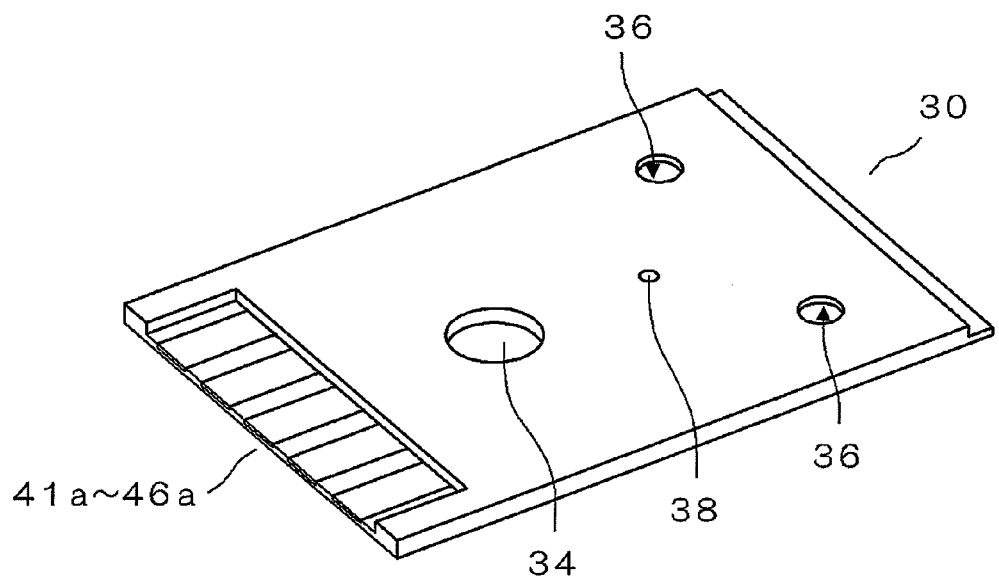
FIG. 8 is an oblique view of the blood sensor 30 pertaining to Embodiment 1.

FIG. 7 is a see-through plan view of the blood sensor 30. FIG. 8 is an oblique view of the blood sensor 30.

As shown in FIGS. 7 and 8, two latching holes 36 are provided at one end of the blood sensor 30. These latching holes 36 are latched to latching protrusions 15h (see FIG. 2A) formed on the sensor mounting part 15b, which fixes the blood sensor 30 to the sensor holder 15.

When the blood 14 flows into the blood inlet 34, the blood 14 is guided by capillary action through the supply path 35, through detecting electrodes 45 and 43, and to the detecting electrode 42, in that order. When the blood 14 is guided to the detecting electrode 42, this tells that enough of the blood 14 has reached the detecting electrodes 41 and 43 constituting the detector 37 in front of the detecting electrode 42. The blood 14 reacts with a reagent 40. The result of this reaction is guided to the connecting electrodes 41a and 43a.

Figure 9:
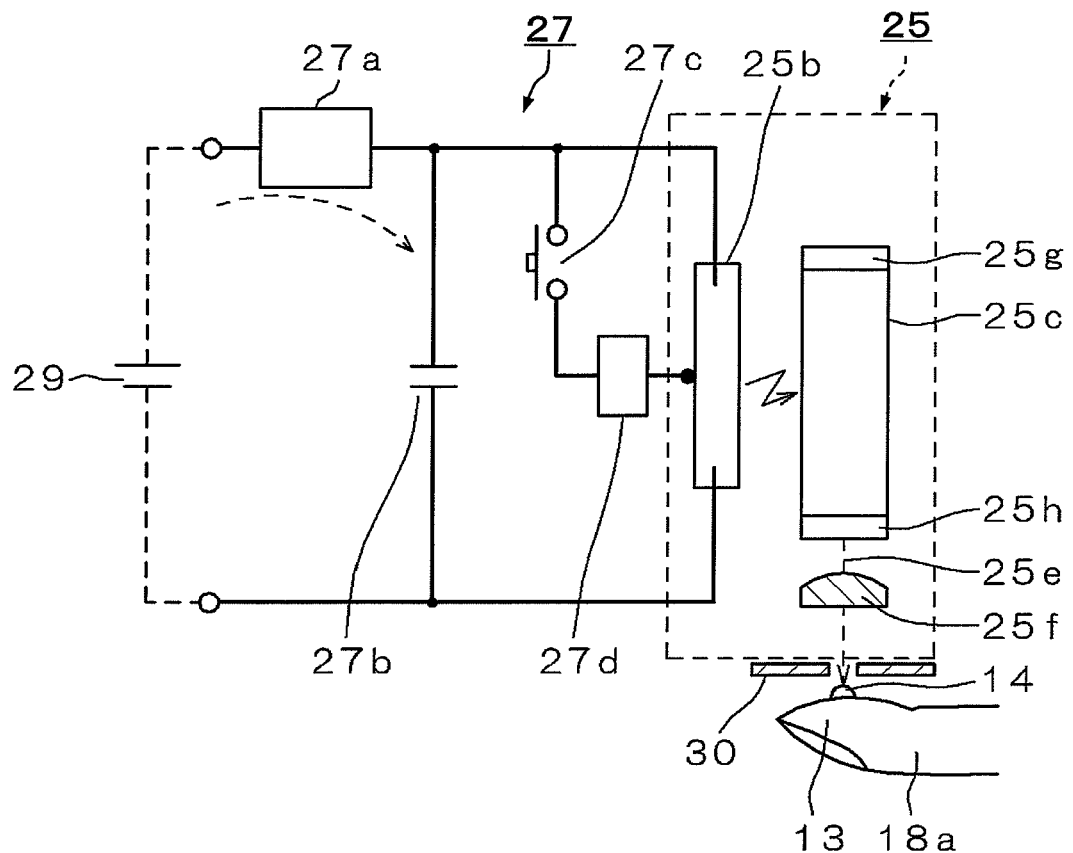
FIG. 9 is a block diagram of a laser puncture unit 25 and a high voltage generation circuit 27 pertaining to Embodiment 1.

FIG. 9 is a block diagram of the laser puncture unit 25 and the high voltage generation circuit 27, which supplies high voltage to the laser puncture unit 25. The high voltage generation circuit 27 comprises a booster circuit 27a connected to the battery 29, a capacitor 27b connected to the output of the booster circuit 27a, a trigger switch 27c connected to the capacitor 27b, and a trigger circuit 27d connected to the output of the trigger switch 27c. The two ends of the capacitor 27b are connected to the electrodes of a lamp 25b constituting part of the laser puncture unit 25. The output of the trigger circuit 27d is connected to a trigger electrode of the lamp 25b.

The capacitor 27b can be one having an electrostatic capacity of 100 to 400 μF (microfarads) and a voltage resistance of 100 to 350 V. An IGBT (insulated gate bipolar transistor) can be used as the trigger switch 27c. The trigger switch 27c is turned on and off by the output of a puncture button 48a (see FIG. 10).

The laser puncture unit 25 comprises the lamp 25b, a laser rod 25c formed from Er:YAG (yttrium-aluminum-garnet) and provided near the lamp 25b, and a lens 25f provided in the laser emission direction of the laser rod 25c. A total reflection film 25g is formed at the end face of the laser rod 25c in the opposite direction from the laser emission direction, and a partial transmission film 25h is formed at the end face in the laser emission direction.

A partial reflection mirror may be disposed instead of the partial transmission film 25h, and a total reflection mirror instead of the total reflection film 25g, rather than forming films at the end faces of the laser rod 25c.

Next, the operation of the laser puncture unit 25 will be described. Voltage supplied from the battery 29 is boosted by the booster circuit 27a and charges the capacitor 27b. The voltage supplied from the battery 29 can be varied by controlling the booster circuit 27a from the outside. This allows the depth of puncture into the first finger 18a to be controlled. The voltage with which the capacitor 27b is charged is supplied to the two electrodes of the lamp 25b. If the puncture button 48a (see FIG. 10) is pressed after this voltage has been boosted to a predetermined level (at least 300 V), the trigger circuit 27d works 0.5 second later, and the lamp 25b emits light. The emission of the lamp 25b excites the Er:YAG in the laser rod 25c and generates the laser beam 25e. The laser beam 25e is amplified while going back and forth through the total reflection film 25g and the partial transmission film 25h, and part of the laser beam 25e goes through the partial transmission film 25h and is outputted to outside the laser rod 25c. The laser beam 25e outputted to outside the laser rod 25c goes through the lens 25f and the blood sensor 30 and punctures the skin 13 of the first finger 18a. The blood 14 oozes out of the skin 13.

Figure 10:
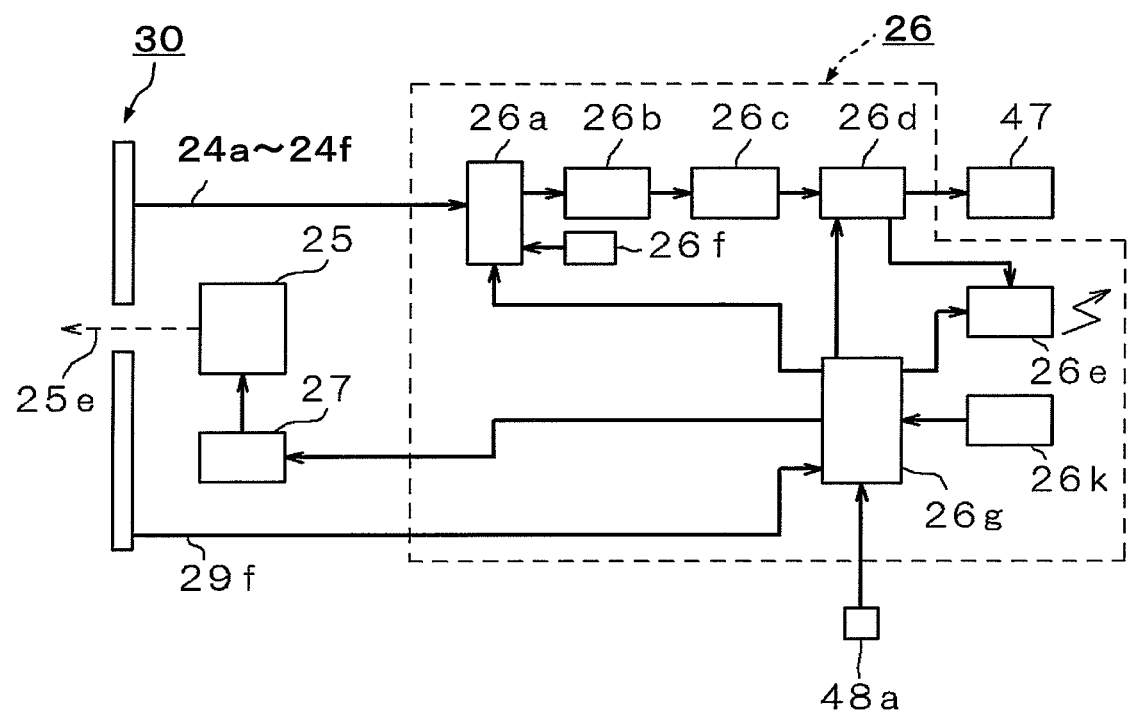
FIG. 10 is a block diagram of the configuration of a measurement circuit 26 pertaining to Embodiment 1, and its surroundings.

FIG. 10 is a block diagram of the measurement circuit 26 and its surroundings. In FIG. 10, the connecting electrodes 41a to 46a of the blood sensor 30 (see FIG. 7) are connected to a switching circuit 26a via contacts 24a to 24f of the connectors 24 (see FIG. 5). The output of the switching circuit 26a is connected to the input of a current/voltage converter 26b. The output thereof is connected to the input of a computer 26d via an analog/digital converter (hereinafter referred to as an A/D converter). The output of the computer 26d is connected to a transmitter 26e and a display 47 formed from liquid crystal. A reference voltage source 26f is connected to the switching circuit 26a.

The output of a controller 26g is connected to the high voltage generation circuit 27 (which is connected to the laser puncture unit 25), the control terminal of the switching circuit 26a, the computer 26d, and the transmitter 26e. The input of the controller 26g is connected to the puncture button 48a, a timer 26k, and a contact 29f (a contact corresponding to the connecting electrode 46a).

Next, the measurement of blood glucose level will be described. First, when the puncture button 48a is pressed, the controller 26g turns on the trigger switch 27c (see FIG. 9) of the high voltage generation circuit 27. When the trigger switch 27c is turned on, the laser beam 25e is emitted from the laser puncture unit 25, and the skin 13 of the first finger 18a is punctured. The puncture of the skin 13 causes the blood 14 to ooze out from the skin 13. Measurement of this oozed blood 14 is then performed.

In the measurement operation, first it is determined whether or not the blood 14 has flowed to all of the detecting electrodes 41 to 45. That is, the switching circuit 26a is switched to connect the detecting electrode 41 to the current/voltage converter 26b. Also, the detecting electrode 42, which serves to detect the inflow of the blood 14, is connected to the reference voltage source 26f. A constant voltage is then applied between the detecting electrodes 41 and 42.

In this state, when the blood 14 flows in, current flows between the detecting electrodes 41 and 42. This current is converted into voltage by the current/voltage converter 26b, and the voltage value is converted into a digital value by the A/D converter 26c. This digital value is outputted toward the computer 26d. The computer 26d detects that enough of the blood 14 has flowed in on the basis of this digital value.

Next, the measurement of glucose, which is a blood component, is carried out. This measurement of the glucose content involves first switching the switching circuit 26a under a command from the controller 26g, so that the detecting electrode 41 (see FIG. 7), which serves as a working electrode for measuring the glucose content, is connected to the current/voltage converter 26b. The detecting electrode 43 (see FIG. 7), which serves as a counter electrode for measuring the glucose content, is connected to the reference voltage source 26f.

Current then flows between the detecting electrodes 41 and 43. This current is converted into voltage by the current/voltage converter 26b, and the voltage value is converted into a digital value by the A/D converter 26c. This digital value is outputted toward the computer 26d. The computer 26d calculates the glucose content on the basis of this digital value.

After measurement of the glucose content, the Hct value is measured. The measurement of the Hct value is performed as follows. First, the switching circuit 26a is switched under a command from the controller 26g. Then the detecting electrode 45, which serves as a working electrode for measuring the Hct value, is connected to the current/voltage converter 26b. The detecting electrode 41, which serves as a counter electrode for measuring the Hct value, is connected to the reference voltage source 26f.

Next, under a command from the controller 26g, a constant voltage is applied between the detecting electrodes 45 and 41 (see FIG. 7) from the current/voltage converter 26b and the reference voltage source 26f. The current flowing between the detecting electrodes 45 and 41 is converted into voltage by the current/voltage converter 26b, and the voltage value is converted into a digital value by the A/D converter 26c. This digital value is outputted toward the computer 26d. The computer 26d calculates the Hct value on the basis of this digital value.

Using the Hct value and glucose content obtained by this measurement, the glucose content is corrected with the Hct value by referring to a predetermined calibration line or calibration line table, and the corrected result is displayed on the display 47. Whether a calibration line or a calibration line table is used is determined on the basis of an identification component 46 inside the blood sensor 30.

The measurement of glucose was described above as an example, but the reagent 40 of the blood sensor 30 may be replaced, and the present invention may be applied to the measurement of a lactate value or blood cholesterol content instead of the measurement of glucose.

Embodiment 2

Embodiment 2 differs from Embodiment 1 in that an opening 52a (corresponds to the opening 22a in Embodiment 1) into which the holder unit 16 is inserted is provided in the middle of the lower edge of a case 52 (corresponds to the case 22 in Embodiment 1). Therefore, the finger on either the one hand 17 or the other hand 18 can be punctured. In the following description of the drawings, those components that are the same as in Embodiment 1 are numbered the same. Also, since the mounting of the parts in the case 52 not discussed below is the same as the mounting of the parts in the case 22 pertaining to Embodiment 1, it will not be described again. The same applies to the other embodiments given below.

Figure 11A:
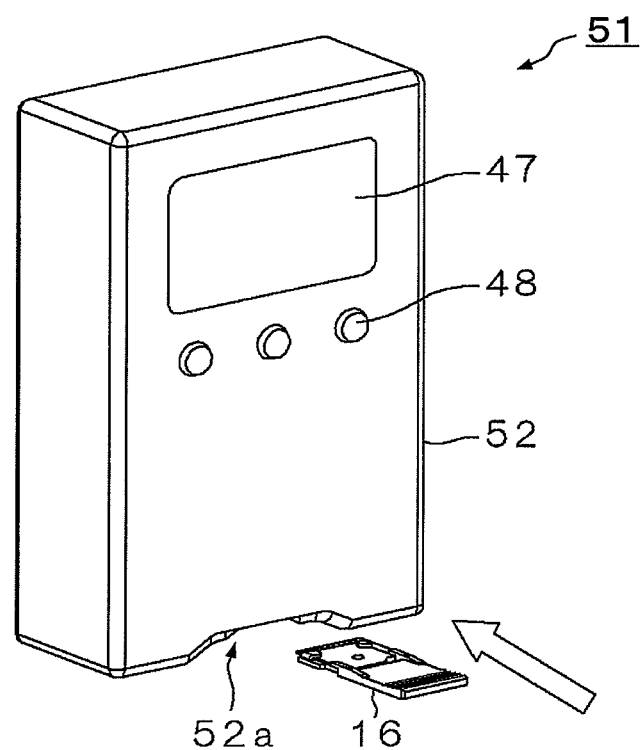
FIG. 11A is an oblique view of a blood testing device 51 pertaining to Embodiment 2, as seen from the front face side.
Figure 11B:
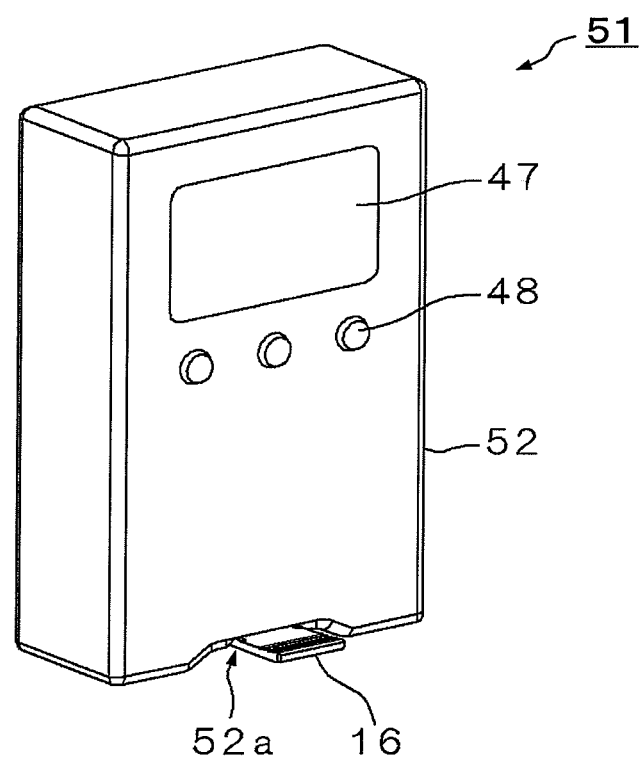
FIG. 11B is an oblique view of the blood testing device 51 pertaining to Embodiment 2, as seen from the front face side.

FIGS. 11A and 11B are oblique views of a blood testing device 51 pertaining to Embodiment 2 (corresponds to the blood testing device 21 in Embodiment 1), as seen from the front face side. More specifically, FIG. 11A shows the state before the holder unit 16 is inserted into the opening 52a. As shown in FIG. 11A, the opening 52a is provided in the middle of the lower edge of the case 52 of the blood testing device 51. Although not depicted, the opening 52a is provided with the holder unit mounting component 23 and connectors 24 just as in Embodiment 1.

FIG. 11B shows the state after the holder unit 16 has been inserted into the opening 52a. As shown in FIG. 11B, the holder unit 16 is inserted into the opening 52a. Consequently, the holder unit 16 is mounted on the holder unit mounting component 23. At this point, the connecting electrodes 41a to 46a of the blood sensor 30 mounted on the holder unit 16 are connected to the connectors 24 (24a to 24f).

Thus, in this embodiment, since the opening 52a is provided in the middle of the bottom edge of the case 52, there is left and right symmetry and a finger can be punctured just as either the one hand 17 or the other hand 18. Therefore, it is unnecessary for just one hand, either the hand 17 or the hand 18, to bear all the burden of puncture. Also, although not depicted, the opening 52a may be provided with a sliding cover to keep out dust and dirt.

Embodiment 3

Embodiment 3 differs from Embodiment 1 in that a cut-out 63 is provided at the lower right corner of a case 62 (corresponds to the case 22 in Embodiment 1), and that an opening 62a (corresponds to the opening 22a in Embodiment 1) into which the holder unit 16 is inserted is provided to the cut-out 63. Therefore, the cut-out 63 forms a larger space above and below the grip 15e of the holder unit 16, and this makes it easier to remove and install the holder unit 16.

Figure 12A:
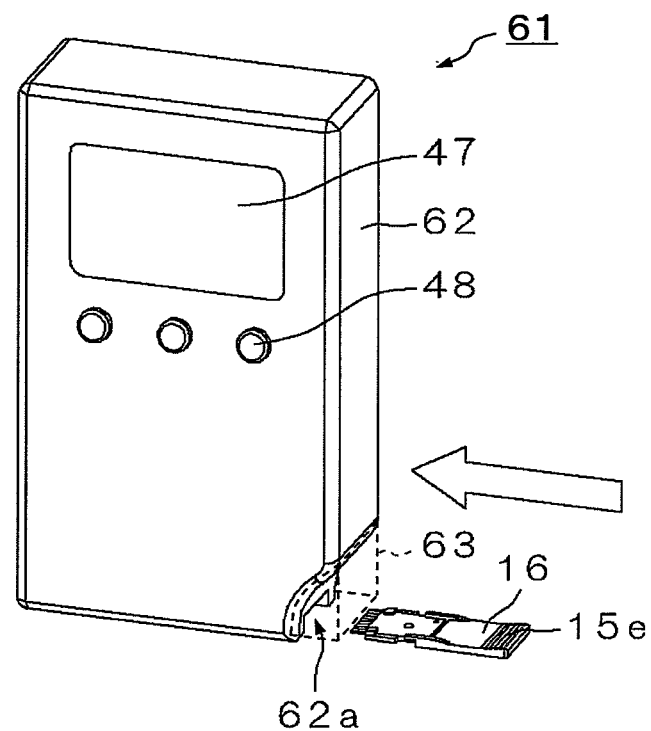
FIG. 12A is an oblique view of a blood testing device 61 pertaining to Embodiment 3, as seen from the front face side.
Figure 12B:
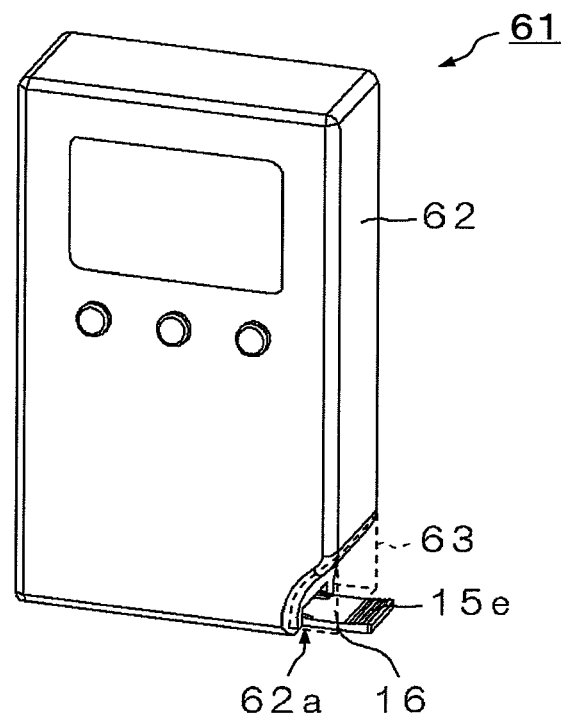
FIG. 12B is an oblique view of the blood testing device 61 pertaining to Embodiment 3, as seen from the front face side.

FIGS. 12A and 12B are oblique views of a blood testing device 61 pertaining to Embodiment 3 (corresponds to the blood testing device 21 pertaining to Embodiment 1), as seen from the front face side. More specifically, FIG. 12A shows the state before the holder unit 16 is inserted into the opening 62a. As shown in FIG. 12A, the cut-out 63 is formed at the lower right corner of the case 62 of the blood testing device 61. Also, the opening 62a is provided on the inside of the cut-out 63, that is, on the side of the cut-out 63 that is at the lower edge of the case 62. Although not depicted, the opening 62a is provided with the holder unit mounting component 23 and connectors 24 just as in Embodiment 1.

FIG. 12B shows the state after the holder unit 16 has been inserted into the opening 62a. As shown in FIG. 12B, the holder unit 16 is inserted through the opening 62a. Consequently, the holder unit 16 is mounted on the holder unit mounting component 23. At this point, the connecting electrodes 41a to 46a of the blood sensor 30 mounted on the holder unit 16 are connected to the connectors 24 (24a to 240.

Thus, in this embodiment, since the opening 62a is provided at the lower edge side of the cut-out 63, the cut-out 63 forms a large space above and below the grip 15e of the holder unit 16. Therefore, it is easier to insert and remove the holder unit 16. Although not depicted, the opening 62a may be further provided with a sliding cover to keep out dust and dirt.

Embodiment 4

Embodiment 4 differs from Embodiment 1 in that an eject button 73 for ejecting a holder unit 81 (corresponds to the holder unit 16 in Embodiment 1) out of a case 72 (corresponds to the case 22 in Embodiment 1) is provided on the right side face of the case 72. Therefore, the holder unit 81 can be ejected out of the case 72 by pressing the eject button 73. There is therefore no need to grasp the grip 15e of the holder unit 81 as the first step in removing the holder unit 81. Specifically, since the grip 15e does not need to stick out from the case 72, the holder unit 81 can be more compact. Also, since part of the holder unit 81 (such as about half of the holder unit 81) can be ejected out of the case 72 by pressing the eject button 73, ejection of the holder unit 81 is extremely simple.

Figure 13:
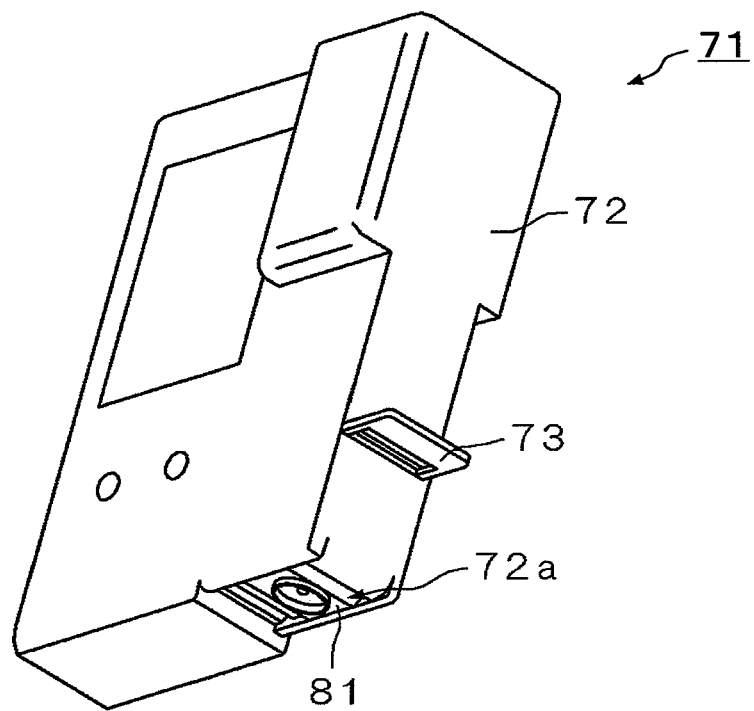
FIG. 13 is an oblique view of a blood testing device 71 pertaining to Embodiment 4, as seen from the bottom face side.

FIG. 13 is an oblique view of a blood testing device 71 pertaining to Embodiment 4 (corresponds to the blood testing device 21 in Embodiment 1), as seen from the bottom face side. The eject button 73 is provided to the right side face of the blood testing device 71, and the holder unit 81 can be ejected out of the case 72 by pressing the eject button 73.

An opening 72a (corresponds to the opening 22a in Embodiment 1) is provided at the lower right corner of the case 72. Although not depicted, the opening 72a is provided with the holder unit mounting component 23 and connectors 24 just as in Embodiment 1.

Figure 14B:
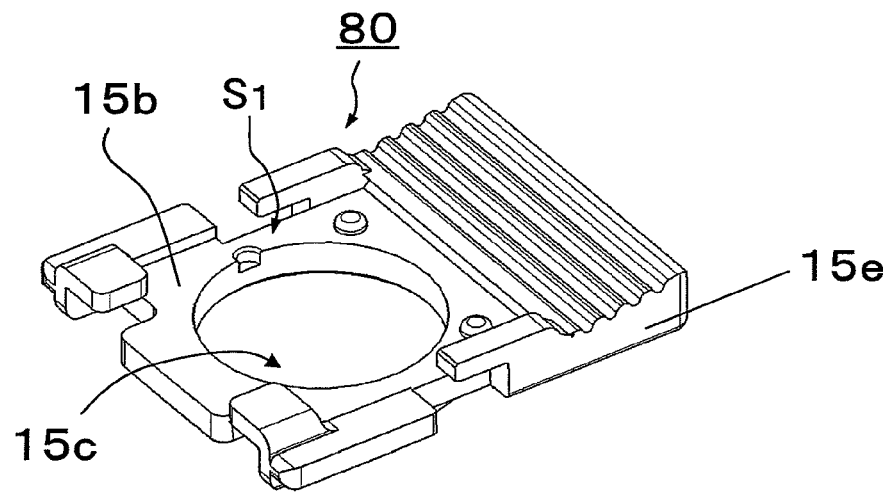
FIG. 14B is an oblique view of a sensor holder 80 pertaining to Embodiment 4, as seen from the first face side.
Figure 14C:
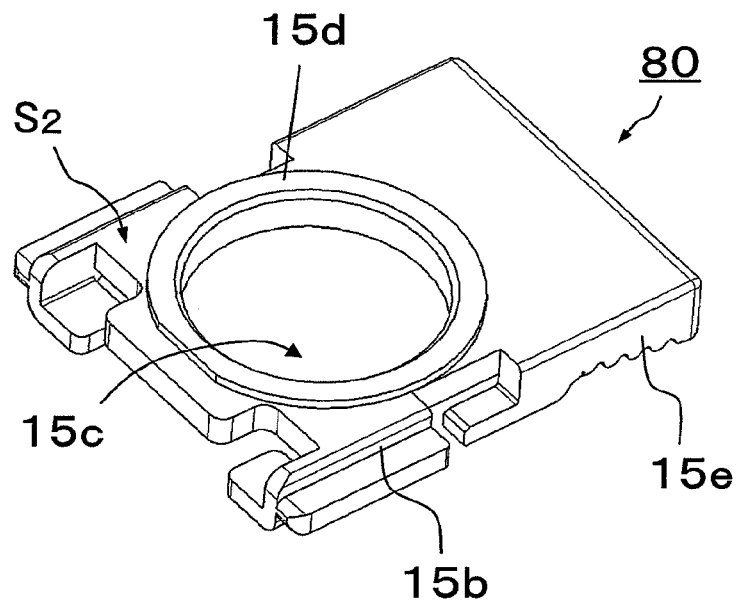
FIG. 14C is an oblique view of the sensor holder 80 pertaining to Embodiment 4, as seen from the second face side.

FIG. 14A is an oblique view of the holder unit 81 pertaining to this embodiment. The holder unit 81 differs from the holder unit 16 described in Embodiment 1 in that it is only about half as long. That is, as shown in FIGS. 14B and 14C, the length of a sensor holder 80 (corresponds to the sensor holder 15 in Embodiment 1) constituting the holder unit 81 is only about half that of the sensor holder 15. The reason why the sensor holder 80 can be made so much smaller is that it is constituted by only the sensor mounting part 15b and the grip 15e, and is not equipped with the main body center part 15a pertaining to Embodiment 1. Furthermore, the through-hole 15c is formed in the sensor mounting part 15b, and the finger holding part 15d is provided on the rear face of the sensor mounting part 15b as shown in FIG. 14C. The above changes allow the holder unit 81 to be more compact.

Figure 15A:
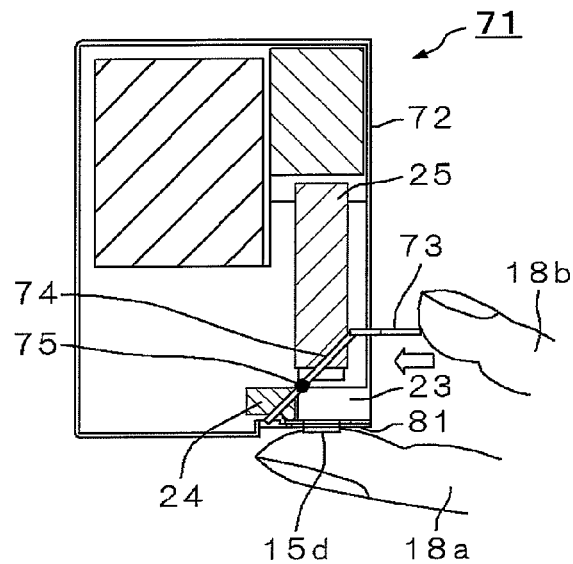
FIG. 15A is a cross section illustrating how to operate the blood testing device 71 pertaining to Embodiment 4.

FIGS. 15A to 15D are cross sections of the blood testing device 71 illustrating how to operate the blood testing device 71. As shown in FIG. 15A, the eject button 73 is provided slidably in the horizontal direction on a side face of the case 72. One end of the eject button 73 sticks out from a side face of the case 72 and comes into contact with the second finger 18b. The other end of the eject button 73 comes into contact with one end of an ejection member 74. The other end of the ejection member 74 comes into contact with one end of the sensor holder 80 (more specifically, the sensor mounting part 15b). The ejection member 74 is provided rotatably around a fulcrum 75 provided in the approximate center of the ejection member 74.

Figure 15B:
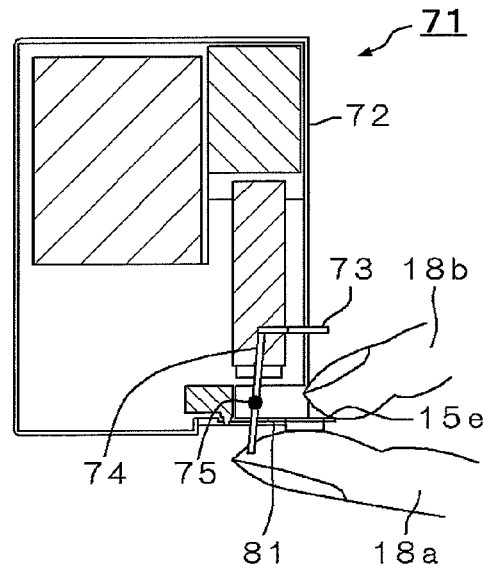
FIG. 15B is a cross section illustrating how to operate the blood testing device 71 pertaining to Embodiment 4.

FIG. 15A shows the state at the completion of puncture of the finger 18a placed against the finger holding part 15d. In FIG. 15A, a thumb 18b is placed against the eject button 73 to eject the holder unit 81. As shown in FIG. 15B, the eject button 73 is pressed by the thumb 18b. In this case, one end of the ejection member 74 is pressed by the eject button 73 and rotates around the fulcrum 75. Thereupon, one end of the sensor holder 80 (more specifically, the sensor mounting part 15b) is pressed by the other end of the ejection member 74, and the holder unit 81 is pushed out of the opening 72a (see FIG. 13).

Figure 15C:
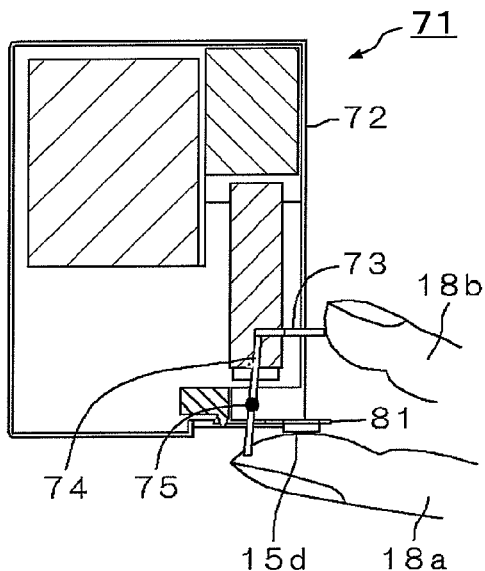
FIG. 15C is a cross section illustrating how to operate the blood testing device 71 pertaining to Embodiment 4.
Figure 15D:
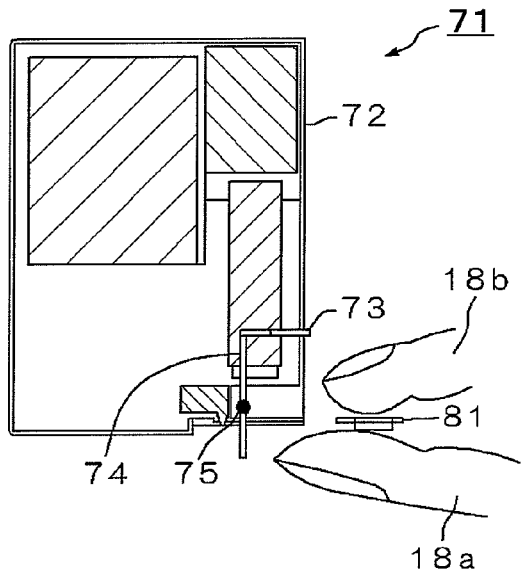
FIG. 15D is a cross section illustrating how to operate the blood testing device 71 pertaining to Embodiment 4.

Then, as shown in FIG. 15C, the grip 15e of the holder unit 81, which has been ejected about halfway from the opening 72a, is gripped and pulled out by the first finger 18a and the second finger 18b. As shown in FIG. 15D, the holder unit 81 held between the first finger 18a and the second finger 18b is then discarded.

Thus, since there is no need to move the first finger 18a from the holder unit 81 in discarding the holder unit 81, it is less likely that the blood 14 that has oozed out due to the puncture will be deposited somewhere else through the movement of the first finger 18a. Therefore, the device can be kept clean and more pleasant to use.

Also, since the holder unit 81 can be formed in a compact size, it can be carried around more easily, and the price can also be kept lower. Although not depicted, the opening 72a may be provided with a sliding cover to keep out dust and dirt.

The invention claimed is:

1. A sensor holder for being removably mounted to a blood testing device having a puncture unit, said sensor holder comprising:
   a sensor mounting part having a first face for placement of a blood sensor, a second face provided on the opposite side of the first face, a through-hole that goes from the first face to the second face and is large enough to allow a puncture tool to pass through, an insertion opening into which the blood sensor is inserted, and a latching protrusion provided on the first face for being latched in a latching hole of the blood sensor;
   a finger holding part that is provided on the second face and surrounds the through-hole on the second face side; and
   a grip that sticks out from the blood testing device when the sensor holder is mounted in the blood testing device, the grip being connected to the sensor mounting part along a first direction,
   wherein the sensor holder has a plate shape which extends along the first direction, and
   wherein the grip has convex portions formed on the first face.

2. A holder unit, comprising:
the sensor holder according to claim 1; and
a blood sensor placed on the first face of the sensor mounting part.

3. A blood testing device, comprising:
a case;
a holder unit mounting component that is provided inside the case;
the holder unit of claim 2 removably mountable to the holder unit mounting component;
a connector for connecting to a connection terminal of the blood sensor;
a puncture unit for puncturing a test subject; and
an electrical circuit connected to the connector.

4. The blood testing device according to claim 3, wherein the holder unit mounting component is provided at one corner of the case.

5. The blood testing device according to claim 3, wherein the holder unit mounting component is provided in the middle of the lower end of the case.

6. The blood testing device according to claim 3, further comprising a cut-out provided at one corner of the case,
wherein the holder unit mounting component is provided on the cut-out side at the lower end of the case.

7. The blood testing device according to claim 3, further comprising an eject button for ejecting the holder unit mounted to the holder unit mounting component,
wherein the holder unit mounting component is provided at one corner of the case.

8. The blood testing device according to claim 3, wherein the puncture unit is provided on an opposite side of the holder unit mounting component from the holder unit.

9. A blood testing device, comprising:
a case;
a holder unit including a blood sensor and a sensor holder which has a plate shape extending along a first direction, the blood sensor having a latching hole, and the sensor holder including:
  i. a sensor mounting part having a first face for placement of the blood sensor, a second face provided on the opposite side of the first face, a through-hole that goes from the first face to the second face, an insertion opening into which the blood sensor is inserted, and a latching protrusion provided on the first face which latches in the latching hole of the blood sensor;
  ii. a finger holding part that is provided on the second face and surrounds the through-hole on the second face side;
  iii. a grip that sticks out from the case when the sensor holder is mounted to the case, the grip being connected to the sensor mounting part along the first direction, and
  iv. wherein the grip has convex portions formed on the first face;
a holder unit mounting component provided inside the case and to which the holder unit is removably mountable;
a connector for connecting to a connection terminal of the blood sensor;
a puncture unit for puncturing a test subject through the through-hole of the sensor holder; and
an electrical circuit connected to the connector.

10. The blood testing device of claim 9, wherein the holder unit mounting component is arranged and configured in the case such that the grip protrudes from the case and the second face of the sensor mounting part faces away from the case when the sensor holder is mounted to the holder unit mounting component,
wherein the puncture unit includes a puncture needle, and
wherein the grip and the convex portions are configured such that removing the sensor holder from the holder unit mounting component displaces the grip and the convex portions relative to the puncture needle.

11. The blood testing device of claim 9, wherein the puncture unit includes a puncture needle which is movable through the through-hole of the sensor mounting part in a first direction, and
wherein the holder unit mounting component is arranged and configured in the case such that the grip protrudes from the case and the second face of the sensor mounting part faces away from the case in the first direction and the convex portions face in a direction opposite to the first direction when the sensor holder is mounted to the holder unit mounting component.

* * * * *